United States Patent [19]

Anthracite

[11] 4,329,995
[45] May 18, 1982

[54] CATHETER FOR NASOTRACHEAL ASPIRATION OF UNCONTAMINATED SPUTUM SPECIMENS

[75] Inventor: Nancy E. Anthracite, San Antonio, Tex.

[73] Assignee: Board of Regents, The University of Texas System, Austin, Tex.

[21] Appl. No.: 182,711

[22] Filed: Aug. 29, 1980

[51] Int. Cl.³ .......................................... A61M 25/00
[52] U.S. Cl. ................................ 128/350 R; 128/4; 128/768; 128/276; 137/843
[58] Field of Search ............. 128/768, 10, 348, 349 R, 128/350 R, 276, 207.18, DIG. 9, 262, 757, 4, 758, 749, 759; 137/843, 853, 844, 859

[56] References Cited

U.S. PATENT DOCUMENTS

| 2,498,692 | 2/1950 | Mains | 128/348 |
|---|---|---|---|
| 3,153,415 | 10/1964 | Sheridan | 128/348 |
| 3,168,092 | 2/1965 | Silverman | 128/1.2 |
| 3,669,099 | 6/1972 | Silverman | 128/2 M |
| 3,788,305 | 1/1974 | Schreiber | 128/2 F |
| 3,874,377 | 4/1975 | Davidson | 128/145.5 |
| 4,023,559 | 5/1977 | Gaskell | 128/348 |
| 4,043,345 | 8/1977 | Kramann et al. | 128/349 R |
| 4,077,610 | 3/1978 | Masuda | 254/134.4 |
| 4,109,659 | 8/1978 | Sheridan | 128/349 R |
| 4,141,364 | 2/1979 | Schultze | 128/349 B |
| 4,147,170 | 4/1979 | Taylor | 128/349 BV |

FOREIGN PATENT DOCUMENTS 2380034 10/1978 France ........................ 128/348

OTHER PUBLICATIONS

Matthew et al., "A Simple Method for Diagnosing Pneumonia in Intubated or Tracheostomized Patients," 5 *Critical Care Medicine* 76, (1977).
Potter et al., "The Bacteriology of the Lower Respiratory Tract," 97 *American Review of Respiratory Disease* 1051, (1968).
Pecora, D., "A Comparison of Transtracheal Aspiration . . . ," *New Eng. J. Med* 664, (Sep. 26, 1963).
Laurenzi et al., "Bacteriologic Flora of the Lower Respiratory Tract," 265 *New Eng. Med.* 1273, (1961).
Lees et al., "Bacteriology of Lower-Respiratory Tract Secretions . . . ", 19 1112, (Dec. 1959).
Wimberly et al., "A Specialized Catheter for Obtaining Specimens Through the Flexible Bronchoscope", Abstract.
Medi-Tech BFW Brush, by Cooper Scientific Corporation.

*Primary Examiner*—Henry J. Recla
*Attorney, Agent, or Firm*—Arnold, White & Durkee

[57] ABSTRACT

A catheter to be passed through the nasopharynx and into the trachea without contamination of the catheter lumen for obtaining uncontaminated sputum specimens. The catheter lumen is sealed to prevent entry of contaminants by the provision of a length of flexible, expandable tubing placed over and attached to the distal end of the catheter. The flexible tubing is rolled-up over a portion of its length and inverted into the unrolled portion, with the unrolled portion forming a cuff encircling the rolled-up portion to hold the rolled portion. A syringe pump connected to the opposite end of the catheter introduces fluid under pressure into the lumen of the catheter to expand the cuff and urge the rolled-up portion of the tubing from the cuff, and to unroll the tubing, whereby the lumen of the catheter is unsealed. An inner catheter is inserted into the lumen of the outer catheter and advanced therethrough and out the end beyond the tubing for performing aspiration.

7 Claims, 5 Drawing Figures

CATHETER FOR NASOTRACHEAL ASPIRATION OF UNCONTAMINATED SPUTUM SPECIMENS

BACKGROUND OF THE INVENTION

The present invention relates to medical instrumentation; and more particularly, it relates to apparatus for obtaining bacteriologic cultures from the lower respiratory tract.

In seeking to identify the pathogenesis of lower respiratory infections in a patient, it is necessary to identify the bacteriologic contents of bronchial secretions. Initially, expectorated sputum was used to indicate the bacteriologic flora of the respiratory tract. However, the sputum may be contaminated by bacteria from the upper respiratory tract during expectoration, which makes evaluation of the brochial bacteriologic cultures misleading.

To obtain uncontaminated samples of brochial secretions, percutaneous transtracheal aspiration has been widely used. In transtracheal aspiration, a small cutaneous wheal is made just below the cricoid cartlidge. A sharp needle is then inserted through the skin, puncturing the trachea. A length of sterilized vinyl tubing is inserted into the trachea through the needle, which is thereafter withdrawn. A sterile syringe attached to the external end of the tubing by a needle provides for aspiration of secretions as the patient coughs. To avoid hematoma and subcutaneous emphysema, pressure must be applied and maintained at the puncture site with a sterilize gauze sponge, both during and for several minutes after the procedure. Although transtracheal aspiration does achieve the result of providing samples of brochial secretions with little contamination, the procedure is not suitable for patients with a high risk of bleeding from thrombocytopenia or coagulation disorders.

Another technique known in the art for obtaining diagnostic samples of bronchial secretions is the so-called "wedge" aspiration technique. In this procedure, a catheter with wire stylet is introduced into the nasopharynx through a larger, softer tube which helps to guide it through the pharynx and reduce contamination. The catheter is advanced as far as possible into the lower airways. The stylet is withdrawn, and a syringe is attached to the catheter and aspiration performed. One recognizes that the catheter has become "wedged" in an airway, by a sense of negative pressure. Positioning of the catheter in a wedged position indicates a closed system in which the catheter samples from the periphery only. After achieving the wedge position, a sample is obtained and the syringe and the catheter withdrawn.

Bronchial secretion samples obtained with the wedge technique are, however, susceptible to contamination by reason of contact of the open ended catheter with the walls of the upper respiratory tract during insertion of the catheter. Accordingly, a gram stain must be made immediately to assess the validity of the specimen obtained. If the gram stain of a specimen reveals a variety of organisms and/or many squamous epithelial cells, the specimen is highly probably contaminated with upper respiratory flora. In such case, the specimen is discarded and a new sample obtained and gram stained. The gram stain is a relative insensitive technique for determining the degree of contamination. The gram stain may appear acceptably uncontaminated on the same sample that the culture is contaminated.

Another technique for obtaining bronchial secretion samples for culturing is that of bronchial swabbing. In this technique, a cotton wool swab on the end of a wire is contained within a glass carrier tube having glass beads fused on the outside surface. The swab and glass carrier tube are passed down a bronchoscope with the swab retracted. The glass beads prevent contact between the open end of the carrier tube and any bronchial secretions present on the inner wall of the bronchoscope. The swab is extended out the open end of the glass carrier tube and the bronchial mucosa is swabbed. After swabbing, the swab is retracted and the glass carrier tube is removed from the bronchoscope. The open distal end of the carrier tube is plugged pending bacteriological examination.

It has been found, however, that the bronchoscope technique, too, allows the bronchial secretion samples to be mixed with bacteria. Accordingly, in a further attempt to obviate the contamination problem, there has been designed a bronchial secretion sampling device for use in conjunction with a fiberoptic bronchoscope. The sampling device consists of inner and outer telescopic catheters adapted for passage through a fiberoptic bronchoscope. The distal end of the outer catheter is capped with a non-toxic water soluble plug. A retractable brush is carried within the inner catheter. To obtain a bronchial secretion sample, the telescoping catheters are advanced beyond the tip of the fiberoptic bronchoscope and the distal plug removed by actuation of the inner catheter. Afterwards, the specimen brush is extended and a specimen obtained. The device is then retracted through the bronchoscope.

Another related technique proposed for obtaining uncontaminated bronchial secretion samples is the use of a small catheter capped with Gelfoam which is introduced through a fiberoptic bronchoscope. The Gelfoam dissolves in the tracheobronchial tree or is coughed up. Although this technique has proven more reliable than other techniques, it suffers from the disadvantage of being relatively expensive since the procedure is performed by a medical specialist using expensive equipment. Accordingly, there is a need for a simple, reliable method and apparatus for obtaining uncontaminated bronchial secretion samples for bacteriologic study.

SUMMARY OF THE INVENTION

In accordance with the present invention, a method and apparatus are provided for obtaining uncontaminated bronchial secretion samples by nasotracheal aspiration.

The apparatus includes an outer catheter having a lumen therethrough for insertion into the lower respiratory tract through the nasopharynx. The apparatus also includes an inner catheter for advancement through the lumen of the outer catheter for performing bronchial aspiration. A length of flexible, expandable tubing is placed over and attached to the distal end of the outer catheter. The tubing is rolled-up over a portion of its length and inverted into the unrolled portion. Inverting the tubing to place the rolled-up proportion into the unrolled portion forms a cuff encircling the rolled-up portion which exerts forces on the rolled-up portion, due to the elasticity of the tubing, which forces support and maintain the rolled-up portion in place such that the lumen of the outer catheter is sealed against entry of foreign matter and contaminants. To unseal the distal end of the outer catheter, means is provided for introducing fluid under pressure into the lumen of the outer catheter to urge the rolled-up portion of the tubing from the cuff and to unroll the tubing. Such fluid pressure introducing means may be a suitable plunger pump, such as an air-filled catheter tip syringe.

The present invention also provides a procedure for obtaining uncontaminated sputum in which a catheter with a sealed end is placed through the nose into the trachea. Thereafter, the end of the catheter is unsealed, and a smaller catheter is advanced through the outer tube and further into a bronchial airway. Aspiration is then performed to obtain bronchial secretion samples for culture and other tests. The procedure avoids the need for having the sample obtained by placing a needle through the trachea or using a complex and expensive bronchoscope procedure.

BRIEF DESCRIPTION OF THE DRAWINGS

A more complete appreciation of the invention may be had by reference to the accompanying drawings, illustrating a preferred embodiment of the invention to be described in detailed, wherein.

DETAILED DESCRIPTION OF A PREFERRED EMBODIMENT

Figure 1:
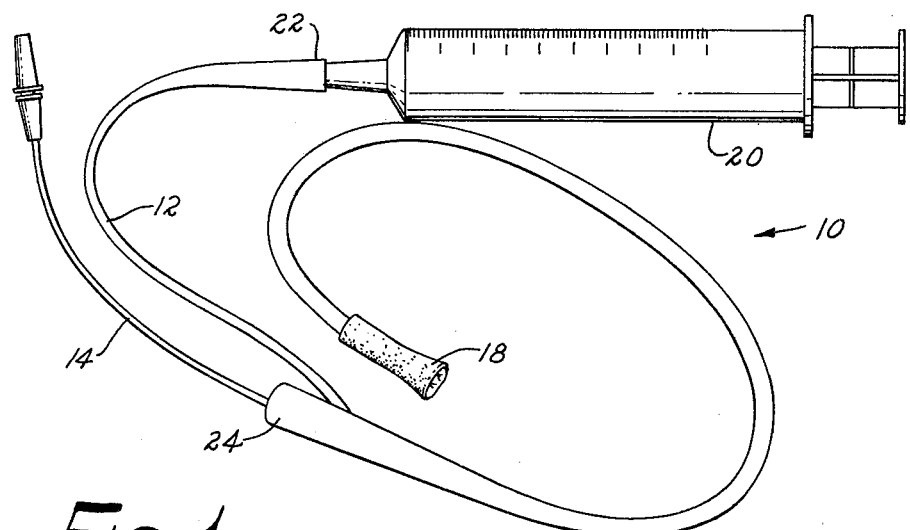
FIG. 1 is an illustration of the nasotracheal catheter ready for use.

Referring to the drawings, and particularly to FIG. 1, there is shown an overall view of the nasotracheal catheter of the present invention ready for use. The illustrated nasotracheal catheter is generally indicated by the reference numeral 10. Nasotracheal catheter 10 comprises an outer catheter 12 adapted for passage into the trachea of a patient. The outer catheter may desirably be an ARGYLE salem sump tube which has been cut off at a length of about 12 inches. Further included is an inner catheter 14 adapted for passage through outer catheter 12 into the main stem bronchi or beyond to provide for withdrawal of bronchial aspirates. Inner catheter 14 may desirably be an INTRACATH catheter with wire stylet. The inner catheter is suitably a 24 inch, 16 gauge catheter.

Nasotracheal catheter 10 further comprises a length of flexible tubing 18 attached to the distal end of outer catheter 12. Tube 18 is rolled-up over a portion of its length and inverted into the unrolled section as shown in FIG. 1. Suitably, the length of flexible tubing is approximately 3½ inches long initially. The tube is rolled tightly for 1 to 1½ inches before it is inverted.

The material for tube 18 may satisfactorily be ¼ inch DAVOL brand Penrose drain tubing. Tubing 18 is prepared by washing and then drying a segment of the drain tubing. Next, the tube segment is gas sterilized and dusted with sodium bicarbonate.

Attachment of tube 18 to outer catheter 12 may be by tying the tube securely with O silk. Moreover, it has been found satisfactory to tie the silk using the tying technique used for splicing the ends of rope; however, any strong tie will be satisfactory. In addition, epoxy cement is placed between the penrose drain and the catheter before the tie is placed. The placement of tube 18 on outer catheter 12 should be such that the rolled-up portion of the tube, when the tube is inverted, is almost touching the tip of outer catheter 12.

As shown in FIG. 1, an air-filled catheter tip syringe 20 is attached to the upper end 22 of outer catheter 12.

Prior to use of nasotracheal catheter 10, tube 18 and a portion of outer catheter 12 are lubricated with water soluble jelly. Passage of outer catheter 12 into the trachea is through the nasopharynx as determined by a patient's inability to talk. Once outer catheter 12 is in place in the trachea, opening 24 of outer catheter 12 is aseptically occluded with the operator's thumb and air from syringe 20 is forced into the outer catheter lumen through the opening at end 22. Air under pressure forces tube 18 to unroll and unseal the passageway through the distal end of outer catheter 12.

Figure 2:
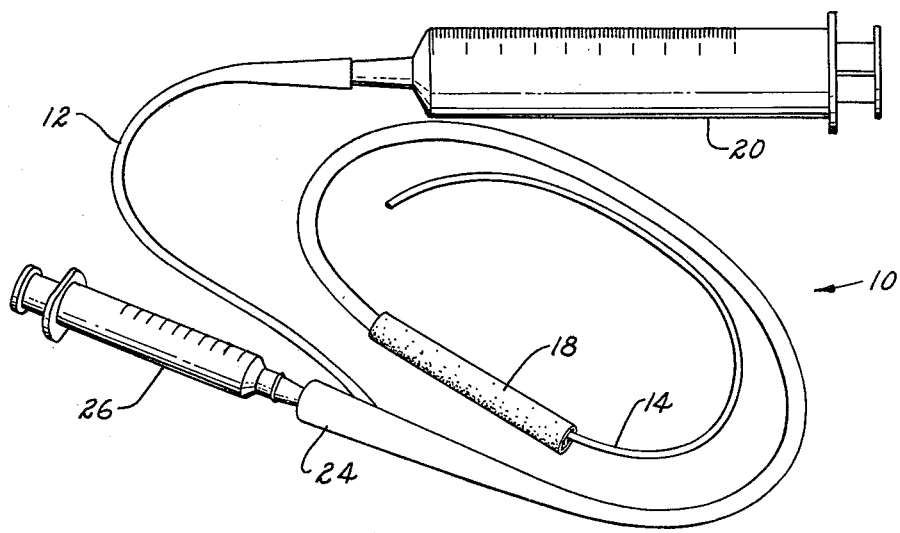
FIG. 2 is an illustration of the nasotracheal catheter, as it would be after passage into the trachea, with the outer catheter lumen unsealed and the inner catheter extended for performing tracheal aspiration.

As shown in FIG. 2, after tube 18 is unrolled, inner catheter 14 may be advanced into the lower respiratory tract for sampling of brochial secretions. A syringe 26 is attached to the upper end of inner catheter 14 to provide for bronchial aspiration sampling.

Figure 3:
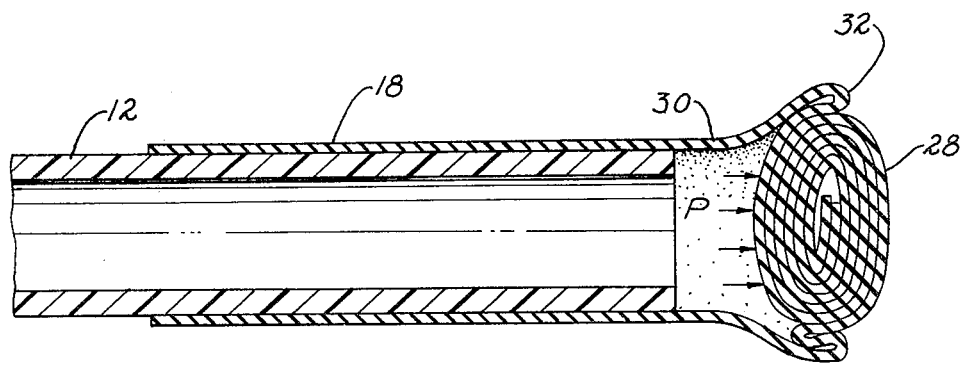
FIG. 3 is a cross-sectional view of the distal end of the outer catheter and the rolled and inverted flexible tubing which seals the outer catheter lumen.
Figure 4:
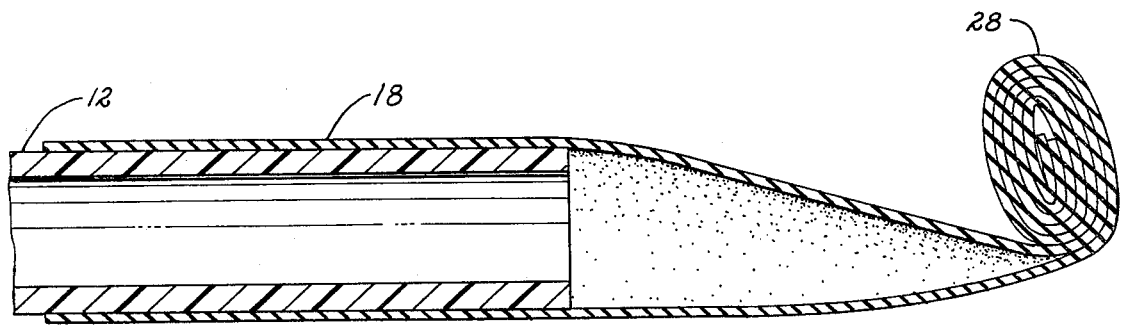
FIG. 4 is a cross-sectional view of the distal end of the outer catheter and the flexible tubing after the rolled-up portion has been urged from the inverted position.
Figure 5:
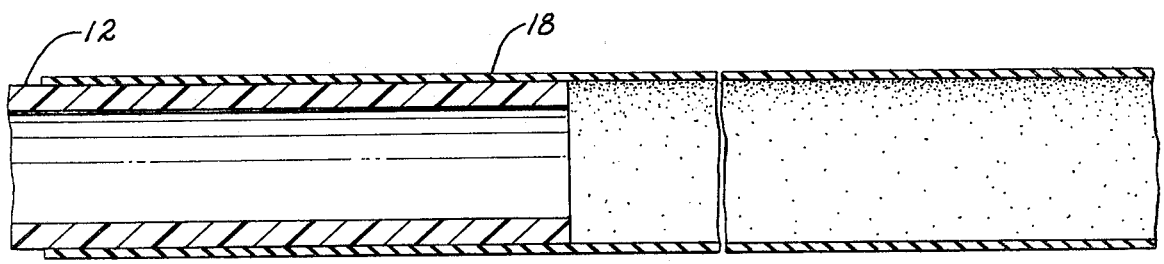
FIG. 5 is a cross-sectional view of the distal end of the outer catheter and the flexible tubing after it is unrolled.

Referring next to FIGS. 3–5, there is shown in greater detail flexible tube 18 and the manner in which it seals and selectively unseals the distal end of outer catheter 12. In FIG. 3, tube 18 is illustrated after it is inverted to place the rolled-up portion 28 into the unrolled portion 30. As indicated, the rolled-up portion 28 is supported and maintained securely within unrolled portion 30. The unrolled portion 30 includes a cuff 32 that encircles the rolled-up portion. Because of the flexibility and elasticity of tube 18, it expands slightly at the cuff 32 and applies an inwardly directly force around rolled portion 28 to hold it in place within the unrolled portion.

To unseal the end of outer catheter 12, as previously described, fluid pressure, such as compressed air, is established within the interior of tube 18. As diagrammed in FIG. 3, fluid pressure creates a force acting against rolled portion 28, urging it out from within the unrolled portion 30. Additionally, fluid pressure established within tube 18 acts along the interior surface wall of tube 18, to create a force that expands tube 18 and counteracts the inwardly directed elastic forces that maintain rolled portions 28 in place.

FIG. 4 illustrates the appearance of tube 18 just after rolled portion 28 has been pushed out of cuff 32. Continued introduction of fluid pressure will rapidly urge the unrolling of tube 18 into the configuration shown in FIG. 5, which unseals the distal end of catheter 12.

The foregoing description of the invention has been directed to a particular preferred embodiment for purposes of explanation and illustration. Although the catheter of the present invention is particularly suitable for nasotracheal aspiration of uncontaminated sputum specimens, the catheter could also be used through an endotracheal tube or in other applications altogether different, such as in the examination of the gastrointestinal tract. Furthermore, the catheter of the present invention could be useful in veterinary medicine for similar purposes. Accordingly, it is to be understood that the present invention admits to other embodiments and employment in other application without departing from the teachings of the invention as defined in the following claims.

What is claimed is:

1. Apparatus for nasotracheal aspiration, which comprises:
    an outer flexible catheter means adapted for passage through the nasopharynx and into the trachea, the catheter having a lumen therethrough;
    a length of flexible tubing having a first section attached to the distal end of the outer catheter, a second section adjacent said first section forming an expandible cuff portion external to the lumen of said outer catheter and a removing section being rolled-up over its length and inverted into said cuff portion external of the outer catheter lumen to seal the lumen of the outer catheter;
    means for introducing fluid under pressure through the lumen of the outer catheter and into the interior of the flexible tubing to expand the cuff portion thereof and cause the rolled-up portion of the tubing to evert and unroll; and
    an inner catheter slidably disposed within the outer catheter for passage through the lumen of the outer catheter and advancement beyond the unrolled flexible tubing to perform bronchial aspiration.

2. The apparatus of claim 1 wherein the fluid pressure introducing means comprises an air-filled catheter tip syringe inserted in the lumen of the outer catheter.

3. The apparatus of claim 1 wherein the unrolled portion of the flexible tubing forms a cuff encircling the rolled-up portion upon inversion of the rolled-up portion into the unrolled portion.

4. The apparatus of claim 1 wherein the inner catheter comprises a catheter with a wire stylet.

5. The apparatus of claim 1 wherein the outer catheter comprises a salem sump tube.

6. In a catheter system including a catheter having a lumen therethrough to the distal end, the improvement comprising:
    a length of flexible tubing having a first section attached to the distal end of the catheter, a second section adjacent said first section forming an expandible cuff portion external to the lumen of said outer catheter and a remaining section being rolled-up over its length and inverted into said cuff portion external of te outer catheter lumen to seal the lumen of the catheter; and
    means for introducing fluid under pressure through the lumen of the catheter and into the interior of the flexible tubing to expand the cuff portion thereof and cause the rolled-up portion of the tubing to evert and unroll, thereby unsealing the catheter lumen.

7. A method of obtaining bronchial secretion samples from a patient, comprising the steps of:
    placing a first flexible catheter, having the lumen thereof sealed at the distal end by a length of flexible tubing having a first section attached to the distal end of the outer catheter, a second section adjacent said first section forming an expandible cuff portion external to the lumen of said outer catheter and a remaining section being rolled-up over its length and inverted into said cuff portion external of the outer catheter lumen to seal the lumen of the outer catheter, through the nasopharynx into the trachea;
    unsealing the lumen of the first catheter by introducing fluid under pressure into the lumen to evert and unroll the tubing;
    advancing a second catheter through the lumen of the first catheter and beyond the unrolled tubing into a bronchial airway; and
    performing aspiration in a bronchial airway using the second catheter.

* * * * *